United States Patent [19]

DeSantis

[11] Patent Number: 4,536,905

[45] Date of Patent: Aug. 27, 1985

[54] ANTI-SNORE PILLOW

[76] Inventor: Damian G. DeSantis, 1911 Greenfield Dr., El Cajon, Calif. 92021

[21] Appl. No.: 582,826

[22] Filed: Feb. 23, 1984

[51] Int. Cl.³ .............................................. A47C 20/00
[52] U.S. Cl. .......................................... 5/434; 5/436; 5/440
[58] Field of Search .................... 5/434, 436, 440, 446, 5/447, 439; 128/76 R, 202.18

[56] References Cited

U.S. PATENT DOCUMENTS

| | | | |
|---|---|---|---|
| 1,194,200 | 8/1916 | Lowder | 5/436 |
| 2,522,120 | 9/1950 | Kaskey et al. | 5/436 |
| 3,757,365 | 9/1973 | Kretchmer | 5/436 |
| 4,118,813 | 10/1978 | Armstrong | 5/436 |

FOREIGN PATENT DOCUMENTS

| | | | |
|---|---|---|---|
| 136170 | 5/1947 | Australia | 5/436 |
| 753552 | 2/1967 | Canada | 5/440 |

*Primary Examiner*—Gary L. Smith
*Assistant Examiner*—Michael F. Trettel
*Attorney, Agent, or Firm*—Charmasson & Holz

[57] ABSTRACT

A pillow for control of the position of a reclining subject which will inhibit snoring. A semi-soft brace is placed above a shoulder slot which causes discomfort to the subject's head in the dorsal position. Discomfort is relieved when subject rests on the side with his or her head tilted slightly forward. This position is conducive to restful sleep and inhibits snoring.

The extensions which form the shoulder slot also provides lateral support with the subject in either the left side or right side position. The pillow can be sized for standard, queen or king sized sets.

5 Claims, 4 Drawing Figures

ANTI-SNORE PILLOW

FIELD OF THE INVENTION

This invention relates to pillow design, and more specifically, to snore inhibiting devices.

BACKGROUND OF THE INVENTION

The phenomenon of snoring has been the object of much study and efforts aimed at prevention. Factors found to favor snoring are a dorsal position, an open mouth and lack of a deep, restful sleep.

Efforts to control snoring have approached these snore favoring factors independently. Control approaches have included self-hypnosis, surgical amputation of the uvula, injection of sclerosing agents into the soft palate, body restraints, and splints to keep the mouth closed.

These control approaches have not been 100% effective or simple and comfortable to use. A deep, restful sleep is difficult with splints and restraints while surgery has not been fully effective.

SUMMARY OF THE INVENTION

The principal and secondary objects of the invention are:
  to provide a pillow to discourage the dorsal position;
  to provide a pillow to encourage resting on one's side with the chin close to the chest;
  to provide a pillow with simple construction; and
  to provide a pillow with lateral shoulder supports.

These and other objects are achieved by providing extensions to a rectangular foam pad to form a shoulder slot and imbedding a stiffening brace in the middle of the foam pad aligned with the slot. The reclining subject lodges the slot and foam pad against the left or right shoulder while resting on his or her side. The stiffening brace encourages movement of the head inward towards the chest. This fetal position is supported laterally by the extensions and is very restful. If, while asleep, the subject tries to shift to a dorsal position, the stiffening brace will cause mild discomfort, forcing the subject to return to the side position. This fetal position generally prevents snoring and encourages a deep sleep.

DESCRIPTION OF THE PREFERRED EMBODIMENTS OF THE INVENTION

Figure 1:
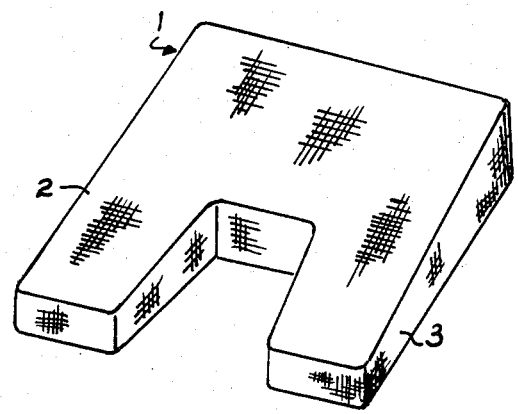
FIG. 1 is a perspective view of an anti-snore pillow.

Referring now to the drawing, FIG. 1 shows an external view of an anti-snore pillow 1. A left and right extension, 2 and 3, form a slot for the shoulder of a reclining subject. The extensions can be formed by cutting the slot from a larger slab of polyurethane foam as shown in FIG. 1, or extensions may be individually formed, and attached to a standard sized pillow or foam pad. The extensions may be tapered to improve comfort, as shown.

Figure 2:
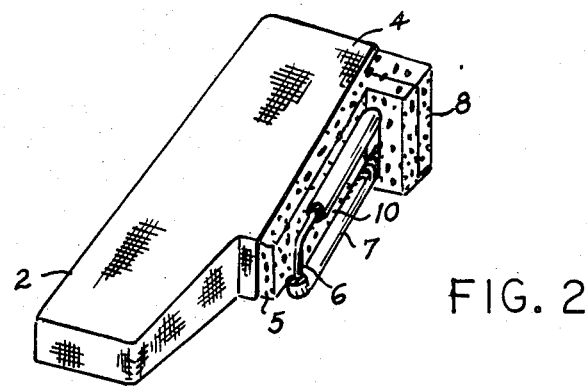
FIG. 2 is a cut-away view of an anti-snore pillow exposing part of the stiffening brace.
Figure 3:
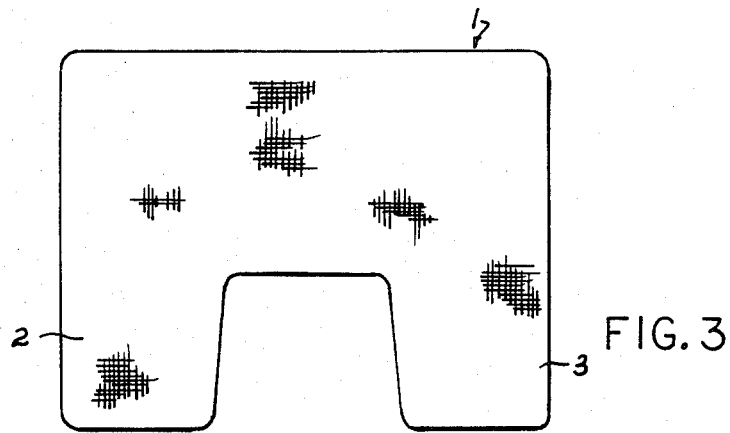
FIG. 3 is a top plan view of the anti-snore pillow.
Figure 4:
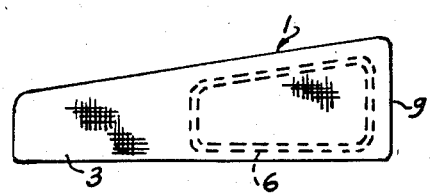
FIG. 4 is a right side view thereof with the relative position of the stiffening rod shown in broken lines.

FIG. 2 shows a cut-away view of a pillow. The cover, 4, is a muslin fabric. The cover 4, surrounds a foam slab, 5, and the extensions 2 and 3. Imbedded in the middle of the foam slab, 5, directly aligned with the slot formed by extensions 2 and 3, is a trapezoidal or rectangular stiffening rod, 6, which is enveloped by semi-soft padding, 7. The stiffening rod, 6, and semi-soft plastic, 7, form a stiffening brace which is fully surrounded by a thin layer of foam to provide minimal comfort. The foam slab, 5, may be foamed in place around the stiffening rod 6, and semi-soft plastic, 7, or the stiffening brace may be placed in a cavity, 10, tunnelled from the back, 9, of the foam slab and covered with filler foam plug, 8. A section of foam in the center of the rectangular stiffening brace is optional. The foam sections and extensions can be attached to the foam slab, 5, using a flexible adhesive.

The semi-soft padding, 7, surrounding the rod, 6, or the entire brace may be made from a plastic material.

While the preferred embodiment of the invention in various configurations has been described, other embodiments and configurations may be devised without departing from the spirit of the invention and the scope of the appended claims.

What is claimed is:

1. A pillow for controlling the position of the head of a reclining subject to prevent snoring which comprises:
   a resilient support pad for said subject's head;
   a pair of extensions of said support pad forming a slot around said subjects shoulders; and
   a stiffening brace imbedded in the middle of said support pad, directly aligned with said slot.

2. The pillow claimed in claim 1 which further comprises a covering for said support pad and pair of extensions.

3. The pillow claimed in claim 2 wherein said support pad comprises a durable non-allergenic polyester foam pad, approximately rectangualar in shape.

4. The pillow claimed in claim 3 wherein said pair of extensions of said support pad comprises durable non-allergenic foam sections, each tapered and rounded, which are joined to said support pad along the longest edge to form a widening slot between said extensions to comfortably contain the shoulders and upper body of a side resting subject.

5. The pillow claimed in claim 4 wherein said stiffening brace comprises a rod covered with semi-soft plastic formed into a rectangular shape, which is imbedded in said support pad in a plane which extends the length of the middle of said slot.

* * * * *